United States Patent [19]
Jagger et al.

[11] Patent Number: 4,781,692
[45] Date of Patent: Nov. 1, 1988

[54] RETRACTABLE SAFETY NEEDLES

[75] Inventors: Janine C. Jagger; Richard D. Pearson; Patrice G. Guyenet, all of Charlottesville, Va.

[73] Assignee: The University of Virginia Alumni Patents Foundation, Charlottesville, Va.

[21] Appl. No.: 30,986

[22] Filed: Mar. 27, 1987

Related U.S. Application Data

[63] Continuation-in-part of Ser. No. 771,640, Sep. 3, 1985, Pat. No. 4,676,783.

[51] Int. Cl.⁴ ............................................. A61M 5/00
[52] U.S. Cl. ................................. 604/164; 604/171; 604/198
[58] Field of Search ............... 604/171, 177, 198, 263, 604/162, 163, 164, 169

[56] References Cited

U.S. PATENT DOCUMENTS

| | | | |
|---|---|---|---|
| 3,055,361 | 9/1962 | Ballard | 604/162 |
| 3,536,073 | 10/1970 | Farb | 604/162 |
| 3,572,334 | 3/1971 | Petterson | 604/162 |
| 3,670,727 | 6/1972 | Reiterman | 604/263 |
| 3,769,975 | 11/1973 | Nimoy et al. | 604/177 |
| 3,906,946 | 9/1975 | Nordström | 604/177 |
| 3,910,272 | 10/1975 | Forberg | 604/162 |
| 4,160,450 | 7/1979 | Doherty | 604/162 |
| 4,362,156 | 12/1982 | Feller, Jr. et al. | 604/177 |
| 4,425,120 | 1/1984 | Sampson et al. | 604/198 |

Primary Examiner—Stephen C. Pellegrino
Attorney, Agent, or Firm—James Creighton Wray

[57] ABSTRACT

A flexible plastic catheter extends from a distal end of a rigid plastic housing. An elastomeric seal at the distal end of the housing tightly fits within the housing and grips in its bore a stylet. The stylet has a sharp distal end and an enlarged proximal end which receives a distal end of a plastic tube within the housing. The stylet is slideable within the elastic seal. In an extended position, the stylet distal end extends beyond a distal end of the catheter and the proximal end abuts the elastomeric seal. In a retracted position, the elastomeric seal grips the catheter near its distal end and the proximal end abuts a constriction in the proximal end of the housing. In that retracted position, the tubing, the stylet and the catheter form a fluid flow path.

13 Claims, 3 Drawing Sheets

RETRACTABLE SAFETY NEEDLES

BACKGROUND OF THE INVENTION

This is a continuation-in-part of Ser. No. 771,640 filed Sept. 3, 1985 now U.S. Pat. No. 4,676,783.

Needlestick injuries are intended to be avoided by properly disposing of needles.

Usually used needles are recapped with the same cover that originally covered the needles before use or by similar covers or tubes before a needle is discarded. That method requires movement of hands toward needles and may promote needlestick injuries during the recapping.

Often needles are disposed of by tossing them into nearby refuse containers, creating danger to those who handle the refuse containers. Usually contaminated needles are placed on trays for carrying to a disposal facility which may be distant from the place where the needles are used. That creates danger en route to persons carrying the trays or pushing carts on which the trays are located or to close by persons who may be injured when the tray slips or spills.

Needle destruction devices are available, but the destructive devices may not be convenient and may be placed permanently at a position that requires the movement of contaminated needles to the destruction devices.

Problems remain in the prevention of needlestick injuries caused by non compliance with established procedures or by inherently unsafe features of the established procedures.

For intravenous (I.V.) catheters, injuries may occur when hospital workers accidently impale themselves on an I.V. catheter stylet after it has been removed from a patient's I.V. catheter. Currently, the devices have no means for safely resheathing the stylet and they are among the items commonly causing needle stick injuries in hospitals.

Another problem associated with the prior art is that of blood backflow following removal of the stylet and before attachment of the catheter to the I.V. tubing. In a conventional system, the catheter is a flexible plastic tube which must be introduced into the patient's vein. A hollow steel stylet runs the length of the catheter to render it rigid. The stylet has a sharp point which protrudes from the distal end of the catheter and enables it to pierce the skin and vein. After introduction of the catheter into the vein, the stylet is withdrawn, set aside, and the I.V. tubing is then connected to the catheter. Backflow of blood occurs when the stylet is removed and blood inadvertently escapes from the catheter port. This is inconvenient, messy, contaminates the environment with patients blood, and makes it necessary for the health care worker to set aside the stylet and join the I.V. tubing to the catheter port as quickly as possible to stem the flow of blood.

SUMMARY OF THE INVENTION

Our new design provides a means for retracting the steel needle/stylet into a rigid housing as the stylet is removed from the patient, thus precluding the possibility of the needle/stylet making contact with the hospital worker.

Our design entirely precludes the backflow of blood because the system remains closed and the stylet is retracted from the catheter but is not withdrawn from the device.

The new design also provides an alternative to the winged steel needle I.V. infusion set in which a steel needle is left in the vein rather than a plastic catheter. The "winged" design is easy to handle and preferred to the I.V. catheter under certain circumstances, but the steel needle may act as an irritant to the vein, requiring frequent removal of the device. In our new design, the indwelling portion of the device is flexible plastic rather than rigid steel, and furthermore, the convenient winged configuration can be retained for ease of handling.

Our intravenous catheter with retractable stylet provides a way to safely withdraw the steel stylet from the catheter without risk of needlestick injury and also precludes the inconvenience and environmental contamination of blood backflow when attaching the I.V. line to the catheter port. The device involves a steel needle bonded to standard clear plastic tubing to form a closed system. The needle/tubing assembly is encased in (but not bonded to) a closely fitting plastic cylinder slightly longer than the length of the needle. Bonded to the plastic cylinder and protruding outward from it, is a plastic catheter. The steel needle is lodged within the catheter to provide rigidity, and the sharp beveled end protrudes from the catheter tip. For use, the catheter/needle portion is inserted through the skin into the vein. When proper placement is complete, the stylet can be retracted into the plastic cylinder by grasping the wing and pulling back on the tubing. The cylinder holds to the stylet/plastic tubing by friction. The stylet is prevented from being pulled too far through the cylinder by a constriction at the bottom end of the cylinder; and prevented from moving out the front of the cylinder by friction. The stylet then lodges in the cylinder for the duration of the use of the device. A rubber gasket at the base of the plastic catheter hugs the stylet just below the beveled point thus allowing the catheter, stylet, and tubing to form a closed, continuous conduit allowing the infusion of I.V. fluids/medications or the withdrawal of blood. The stylet then remains encased in the plastic cylinder and when the device is removed from the patient it is not exposed and can therefore not cause an inadvertent puncture wound. Because it is not necessary to withdraw the stylet from the device, as in the currently employed device, the problem of backflow of blood during connection of I.V. tubing is obviated. Furthermore, because the steel stylet does not remain as an irritant in the vein, the new device may be preferable to the current winged steel needle I.V. infusion sets under certain circumstances.

An intravenous needle with a sharpened distal end has a proximal end fixed within a first enlarged end of an inner tube. The enlarged end of the inner tube is held tightly within a first end of an outer tube by friction. The needle passes through a constricted opening in the first end of the outer tube. The second end of the inner tube passes through a constricted opening in the second end of the outer tube. The needle is used by gripping soft plastic wings on the outer tube and removing a needle cover from a nipple on the first end of the outer tube. The needle is then inserted in the desired location and the outer tube and a protruding end of the inner tube are taped in place. Fluids are permitted to flow through the inner tube and needle. When use is complete, the needle is removed from the vein, the protruding end of the inner tube is pulled outward, pulling the first end of the inner tube and the needle into the outer tube. The first end of the innre tube tightly wedges within the second end of the outer tube, holding the needle totally within the outer tube. Finally, the retracted used needle assembly is discarded, encased in the outer tube.

An intravenous administration system has a retractable safety needle. A steel needle intravenous administration device provides a way to safely resheath contaminated intravenous needles to reduce the risk of accidental needlestick injuries to health care personnel. The device uses a steel needle bonded to standard clear plastic tubing to form a closed system. The needle/tubing assembly is encased in, but is not bonded to, a closely fitting plastic cylinder slightly longer than the length of the needle. The needle protrudes from one end of the cylinder. The cylinder has two small wings at the sides for easy manipulation of the needle. A plastic tab is bonded to the tubing at a position spaced from the cylinder. After the intravenous device is removed from the patient, the contaminated needle is retracted into the plastic cylinder by grasping the wing and pulling axially on the tab. The cylinder grips the plastic tubing by friction which is sufficient to keep the needle from withdrawing during insertion of the device. The grip is overcome, allowing the needle to be pulled into the cylinder, when appropriate force is applied. The needle is prevented from being pulled too far through the cylinder by a constriction at the second end of the cylinder and is prevented from moving out of the first end of the cylinder by friction. The cylinder serves as a protective barrier, protecting hospital personnel from hazardous contaminated needles.

A disposable medical needle apparatus comprises an outer tube and an inner tube mounted in a concentric friction fit relationship. An intravenous needle has a sharpened distal end and a proximal end. The proximal end of the needle is tightly gripped within a first end of the inner tube, and the needle extends outward therefrom through a first constricted opening in a first end of the outer tube. A second end of the inner tube extends outward through a second constriction in the second end of the outer tube. First gripping means on the outer tube provides for gripping the outer tube and second gripping means on the second end of the inner tube provides for gripping the inner tube when sliding the inner tube and needle axially in the outer tube. Connection means on the second end of the inner tube connects the inner tube to a fluid supply.

Preferably, the second constriction in the second end of the outer tube comprises wedge shaped means opening toward the first end of the outer tube for clamping the first end of the inner tube when the second gripping means is pulled in an axial direction away from the outer tube.

In a preferred embodiment, the first end of the inner tube comprises an enlarged head for tightly gripping an inner wall of the outer tube and for preventing outward passage of the first end of the inner tube beyond the second constriction at the second end of the outer tube when the second gripping means pulls the inner tube axially in the outer tube.

Preferably, the first gripping means comprises a soft plastic wing extending outward from the outer tube, and the second gripping means comprises a plastic tab extending outwardly from the second end of the inner tube.

Preferably, the first gripping means comprises soft plastic wings extending oppositely from the outer tube, and the second gripping means comprises plastic tabs extending oppositely from the second end of the inner tube.

In a preferred embodiment, a nipple extends axially on the first end of the outer tube and a tubular plastic cover connected to the nipple extends axially therefrom over the needle and beyond the sharpened distal end of the needle for covering the needle prior to use.

A preferred method of using intravenous needles comprises holding an inner tube fixed within an outer tube, extending a needle from a proximal end fixed within a first end of the inner tube through a constricted opening in a first end of the outer tube, gripping the outer tube and pushing a sharpened distal end of the needle into the desired position, flowing fluids through the inner tube and the needle, discontinuing the flow of fluids through the inner tube and the needle, removing the needle from the vein, protruding a second end of the inner tube through a constricted opening in the second end of the outer tube, gripping the second end of the inner tube and pulling the first end of the inner tube and the needle axially within the outer tube, tightly engaging the first end of the inner tube with the second end of the outer tube and holding the needle within the outer tube.

These and other objects and features of the invention are apparent in the disclosure which includes the above and ongoing specifications with the claims and the drawings.

DETAILED DESCRIPTION OF THE DRAWINGS

Figure 1:
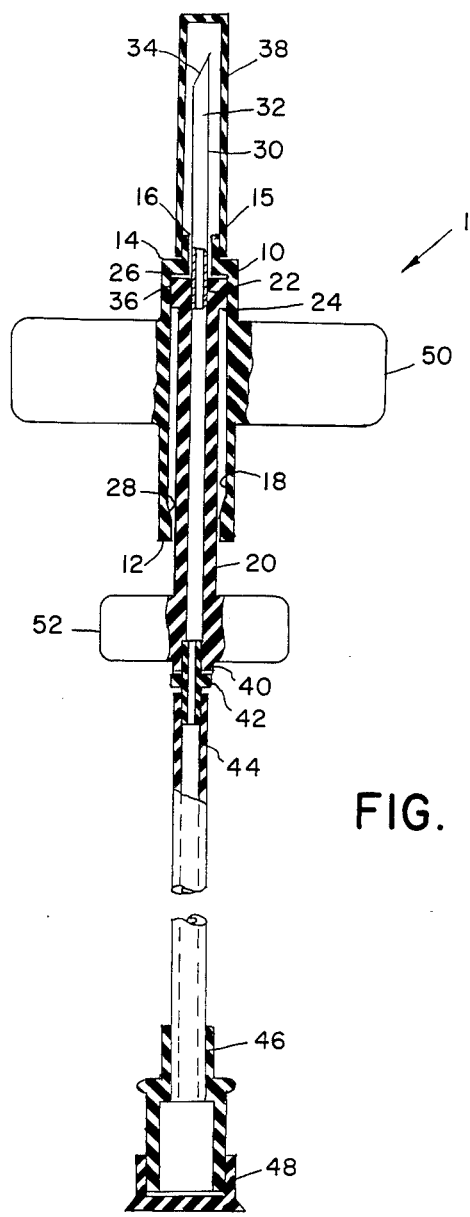
FIG. 1 is an elevational view partly in section of the intravenous needle assembly of the present invention.

Referring to FIG. 1 a needle assembly of the present invention is generally indicated by the numeral 1. A cylinder 10 has two ends 12 and 14 with restricted openings. The first end 14 has a projecting nipple 15 with a constriction 16 in a form of a restricted axial opening. The inner cavity 18 of the cylinder 10 slidingly receives inner tube 20 while gripping the enlarged first end 22 of the inner tube. The outer surface 24 of the enlarged end 22 is tightly gripped by the inner surface 26 at the first end of cavity 18 to hold the unused needle in a protruded usable condition. The second end of the cavity 18 is in a form of a wedge-shaped constriction 28 which tightly grips the outer surface 24 of the enlarged end 22 of tube 20 when tube 20 is pulled rearward or downward as shown in FIG. 1. The gripping of the enlarged end 22 within the wedge 28 holds the needle 30 entirely within the outer tube 10 preventing accidental contact with the needle 30, its shaft 32, or its sharpened distal end 34. The proximal end 36 of the needle is tightly gripped within the first end 22 of the inner tube 20. A protector tube 38 is held on the nipple 15 to prevent accidental contact with the protruded needle 30 before the needle is used.

The second end 40 of the inner tube 20 is provided with a connector 42 for connection to an elongated flexible connector tube 44 which is provided on its distal end with a connector 46 for connecting tube 44 to a supply tube connected to a fluid container. Cap 48 protects the connector 46 before it is used.

Figure 2:
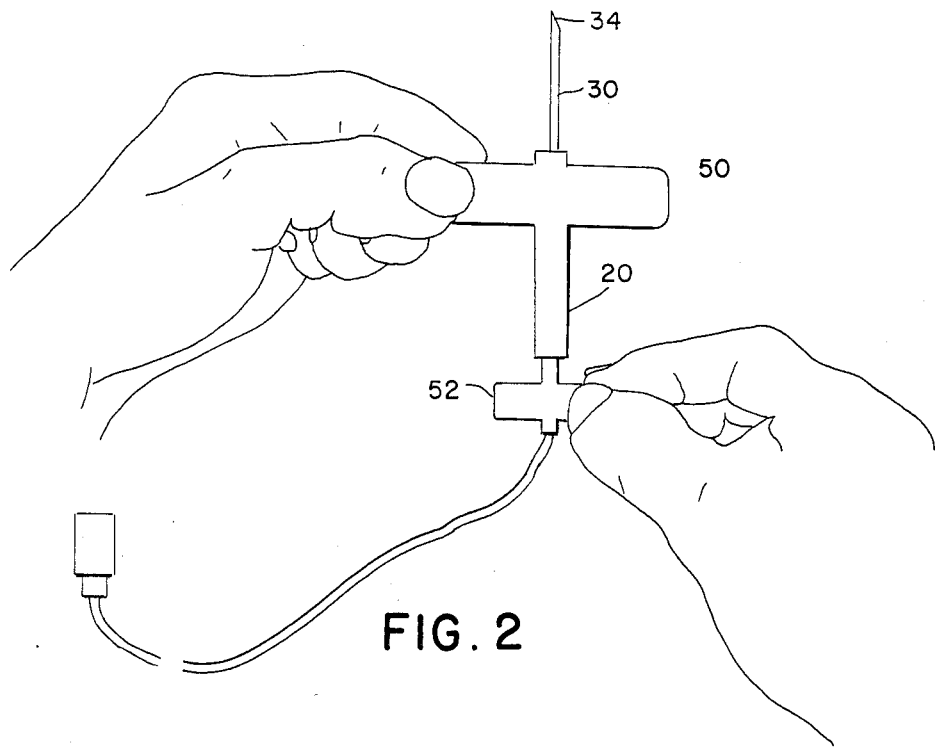
FIG. 2 is a view showing the gripping of the elements for retracting the needle.
Figure 3:
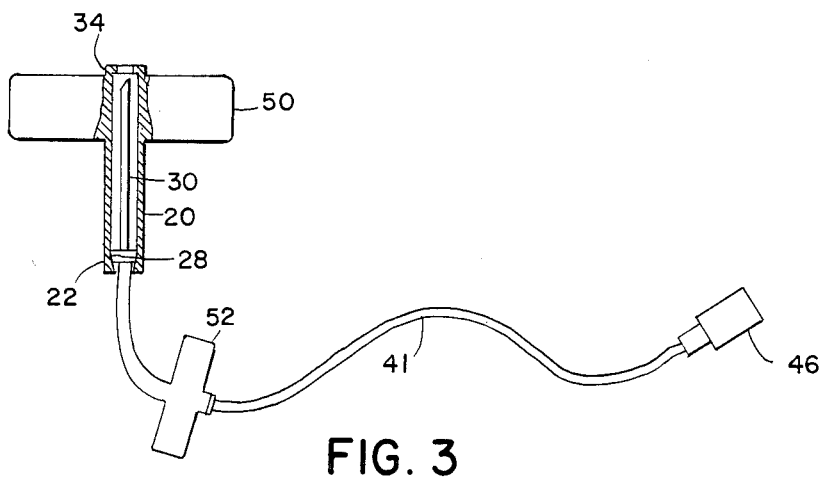
FIG. 3 is a view partially cut away showing the retracted needle in the protective cylinder.

In use, one grips wings 50 and then removes the tubular cover 38 from the nipple 16. Gripping the wings 50, one slides the needle into its desired position. After the needle has been used, wings 50 and tabs 52 are gripped separately as shown in FIG. 2, and tabs 52 and tube 20 are pulled in an axial direction away from wings 50, extending tube 20 from outer tube 10 and pulling needle 30 and sharpened distal end 34 into the outer tube as shown in FIG. 3. The enlarged first end 22 of the inner tube 20 is firmly gripped by the inner wedge surface 28, preventing further relative movement between needle 30 and the outer protective tube 10, as shown in FIG. 3.

Figure 4:
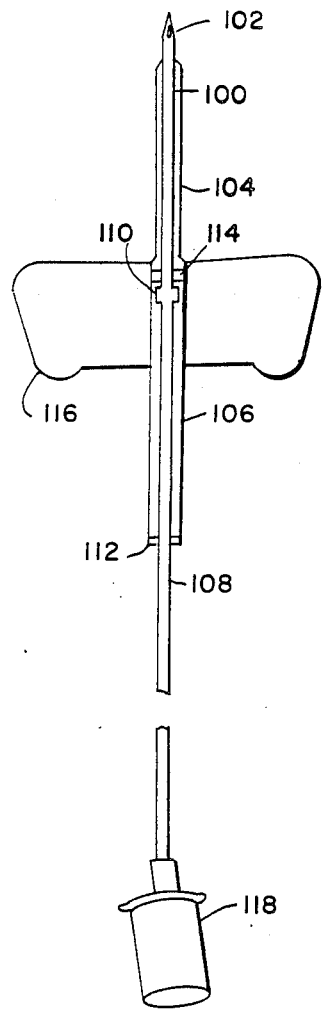
FIG. 4 is a sectional view of a preferred intravenous catheter with retractable stylet.
Figure 5:
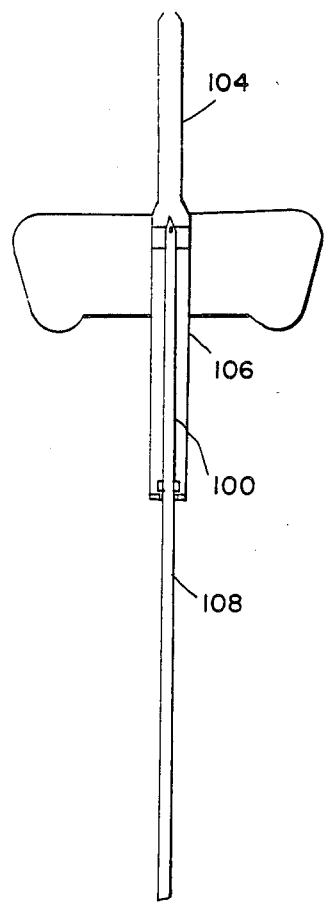
FIG. 5 is the same view as FIG. 4 with the stylet in a retracted position.

Referring to FIGS. 4 and 5, an intravenous catheter is shown in unretracted and retracted states. In the unretracted state, which is the condition of the catheter prior to insertion into a body, the stylet 100 has an end portion 102 that extends a short length beyond an end of catheter 104. Catheter 104 is made of flexible plastic material and is connected to a rigid plastic housing 106. The connection of the catheter to the housing may be by any suitable means including adhesive bonding.

A length of fluid conduit or tubing 108 is connected to a proximal end of the stylet 100. The tubing 108 is flexible and may have a diameter substantially the same as the stylet such that when the metal stylet is inserted into the tubing, an enlarged diameter portion 110 is created.

The housing is provided with a restriction 112 at a proximal end thereof and a seal 114 is provided within the housing at a distal end thereof. The housing is also provided with grips 116 which facilitate use of the catheter as will be described later. The opposite end of the tubing 108 can be provided with an adaptor 118 to facilitate the introduction of fluid into the tubing.

Initially, the stylet punctures the body with the exposed sharpened tip 102 so that the catheter 104 can be introduced into the body as well. After the initial puncture, the stylet 100 is withdrawn from the catheter 104 by pulling the tubing 108. Withdrawal of the stylet is limited by an abutment of the joint 110 and the constriction 112, as shown in FIG. 5. In the fully withdrawn position illustrated in FIG. 5, a seal is created between housing 106 and the stylet 100 such that fluid flows between the catheter 104, the stylet 100 and the tubing 108 and completely bypasses the housing 106. After use, the catheter is withdrawn from the body and the assembly can be discarded with the stylet encased in rigid plastic, thereby posing no danger of accidental needlestick to persons handling the assembly.

While the invention has been described with reference to specific embodiments, modifications and variations may be constructed without departing from the scope of the invention.

The scope of the invention is defined in the following claims.

We claim:

1. An intravenous catheter with retractable stylet comprising, a stylet having a body-insertable distal end and a proximal end connected to a length of flexible plastic tubing, a rigid plastic housing encases the entire stylet when the stylet in a retracted position, a flexible plastic catheter, connected to a distal end of the housing, of length sufficient to substantially cover and be supported by the stylet in a non-retracted position, sealing means, positioned within the distal end of the housing, for sealing the housing by engaging the stylet when the stylet is in extended or retracted position, and abutment means for limiting travel of the stylet.

2. The device of claim 1 wherein the abutment means comprises an increased diameter joint between the stylet and the flexible plastic tubing for contacting a proximal end of the housing when the stylet is in retracted position.

3. The device of claim 2 wherein the joint abuts a constriction at the proximal end of the housing to prevent rearward withdrawal of the stylet from the housing.

4. The device of claim 3 wherein the joint abuts the sealing means at the distal end of the housing to prevent forward movement of the stylet beyond the catheter.

5. The device of claim 1 wherein the sealing means comprises an elastomeric seal tightly fitted in the housing and having a bore slideably receiving the stylet.

6. The device of claim 1 further comprising grip means connected to the housing for gripping the housing while pulling the tubing.

7. A method of using an intravenous catheter comprising, inserting a stylet into a body, wherein the stylet supports a flexible catheter and is connected to fluid conduit, withdrawing the stylet into a rigid housing connected to the catheter by pulling the fluid conduit, and sealing a fluid flow path consisting of the catheter, the stylet, and the fluid conduit with a sealing means which engages the stylet and which is disposed in a distal end portion of the rigid housing.

8. The method of claim 7 further comprising, withdrawing the catheter from the body and discarding the catheter with the stylet encased in the housing.

9. Catheter apparatus comprising a rigid plastic housing having distal and proximal ends, a flexible plastic catheter connected to the distal end of the housing and extending axially therefrom, a stylet having a body-insertable distal end and a proximal end connected to a length of flexible plastic tubing, the stylet being movable within the housing and catheter between an extended position in which a distal end of the stylet projects from a distal end of the catheter and a retracted position in which a distal end of the stylet is positioned within the rigid plastic housing, and a sealing means positioned within a distal end of the housing and engaging the stylet and tightly sealing the distal end of the housing or the stylet in extended and retracted positions of the stylet.

10. The catheter apparatus of claim 9 wherein the sealing means comprises an elastomeric seal tightly fitted in the distal end of the housing and having a bore slideably receiving the stylet.

11. The catheter apparatus of claim 9 wherein the sealing means tightly seals the stylet near its distal end while the stylet is in the retracted position, forming a fluid flow path which consists of the stylet and the catheter in exclusion of the housing.

12. The apparatus of claim 9 further comprising a flexible tubing connected to a proximal end of the stylet and wherein a fluid flow path is formed consisting of the tubing, the stylet and the catheter when the catheter is in its retracted position within the housing.

13. The apparatus of claim 12 wherein the tubing is connected to a proximal end of the stylet within the housing.

* * * * *